(12) United States Patent
Thomas et al.

(10) Patent No.: US 9,498,507 B2
(45) Date of Patent: Nov. 22, 2016

(54) ANTIVIRAL COMPOSITION

(75) Inventors: Becky Mary Thomas, Mumbai (IN);
Arvind Saklani, Mumbai (IN);
Natasha Kapoor, Mumbai (IN); Arno Appavoo Enose, Mumbai (IN); Satish Namdeo Sawant, Mumbai (IN); Ritu Kaushik, Mumbai (IN); Rupa Bhowmick, Mumbai (IN); Ashish Malani, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 653 days.

(21) Appl. No.: 13/985,687

(22) PCT Filed: Feb. 13, 2012

(86) PCT No.: PCT/IB2012/050631
§ 371 (c)(1),
(2), (4) Date: Aug. 15, 2013

(87) PCT Pub. No.: WO2012/110932
PCT Pub. Date: Aug. 23, 2012

(65) Prior Publication Data
US 2013/0323341 A1 Dec. 5, 2013

Related U.S. Application Data

(60) Provisional application No. 61/442,883, filed on Feb. 15, 2011.

(51) Int. Cl.
*A01N 65/00* (2009.01)
*A61K 36/60* (2006.01)

(52) U.S. Cl.
CPC ........... *A61K 36/60* (2013.01); *A61K 2236/00* (2013.01)

(58) Field of Classification Search
CPC ..................................... A61K 36/00
USPC ....................................... 424/725
See application file for complete search history.

(56) References Cited

FOREIGN PATENT DOCUMENTS

WO 2006/078848 A1 7/2006
WO 2010/035226 A2 4/2010

OTHER PUBLICATIONS

Musci I et al: "Combined Effects of Flavonoids and Acyclovir Against Herpesviruses in Cell Cultures", Acta Microbiologica Academiae Scientiarum Hungarica, Sciences, Budapest, vol. 39, No. 2, Jan. 1, 1992, pp. 137-147. XP002074629, ISSN: 0231-4622 abstract; tables.

Blondel O et al: "Insulin resistance in rats with non-insulin-dependent diabetes induced by neonatatl (5 days) streptozotocin: Evidence for reversal following phlorizin treatment". Metabolism. Clinical and Experimental. W.B. Saunders Co., Philadelphia. PA. US. vol. 39. No. 8. Aug. 1, 1990, pp. 787-793. XP0323031758. ISSN: 0026-0495. DOI: 10-1016/0026-0495(90)90120-2 [Retrieved on Aug. 1, 1990] Abstract; p. 788. col. 1. Paragraph 2-col. 1, Paragraph 3.

Mazumder P M * et al: "Hypoglycaemic effect of Ficus arnottiana Miq. bark extracts on streptozotocin induced diabetes in rats". Medicinal & Aromatic Plants Abstracts. Scientific Publishers. Scientific Publishers. New Delhi—India, vol. 32. No. 1, Feb. 1, 2010. XP018028434, ISSN: 0250-4367 the whole document.

Shubhangi Pawar and D A Patil 1*: "Observations on folkloric medicinal plants of Jalgaon district Maharashtra", Indian Journal of Traditional Knowledge, Resources. New Delhi—India, vol. 3. No. 4. Oct. 1, 2004, pp. 437-442. XP018000048, No. 13.

Sheu Va-Wen et al: "Cytotoxic flavonoids and new chromenes from *Ficus formosana* f. *formosana*". Planta Medica. vol. 71. No. 12. Dec. 2005. pp. 1165-1167. XP009159573. ISSN: 0032-0943 the whole document.

*Primary Examiner* — Michael Meller
(74) *Attorney, Agent, or Firm* — Ladas & Parry LLP (57) ABSTRACT

The present invention relates to a composition comprising extract of the plant *Ficus arnottiana*. The invention also relates to a process for the preparation of the composition and to the composition for the use in the treatment of viral infections, particularly caused by herpes simplex viruses (HSV). The invention further relates to a method of treating a viral infection in a mammal comprising administering to the mammal a therapeutically effective amount of the composition.

11 Claims, 5 Drawing Sheets

ANTIVIRAL COMPOSITION

RELATED APPLICATION INFORMATION

This application is a 371 of International Application PCT/IB2012/050631 filed 13 Feb. 2012 entitled "Antiviral Composition", which was published in the English language on 23 Aug. 2012, with International Publication Number WO 2012/110932 A1, and which claims priority from U.S. Patent Application 61/442,883 filed 15 Feb. 2011, the content of which is incorporated herein by reference.

FIELD OF THE INVENTION

The present invention relates to a composition comprising an extract of the plant *Ficus arnottiana* having an antiviral activity. The invention also relates to a process for the preparation of the composition. The invention further relates to the composition for use in the treatment of viral infections, particularly those caused by herpes simplex viruses (HSV).

BACKGROUND OF THE INVENTION

Viruses are the etiological cause of many life-threatening or life impairing human diseases. Of special concern are herpes viruses such as herpes simplex virus type 1 (HSV-1), herpes simplex virus type 2 (HSV-2), cytomegalovirus (CMV), Epstein-Barr virus (EBV), varicella zoster virus (VZV), and human herpes viruses 6, 7 and 8 (HHV-6, HHV-7 and HHV-8) and the like.

Herpes simplex is a viral disease caused by herpes simplex viruses (HSV). HSV-1 is commonly associated with facial herpes known as cold sores or fever blisters. HSV-1 infection generally occurs in the oropharyngeal mucosa wherein the trigeminal ganglion becomes colonized and harbors latent virus. HSV-2 is more often associated with genital herpes. HSV-2 usually spreads sexually and occurs in the anus, rectum, upper alimentary canal as well as the genital area with seeding of the sacral ganglia. Depending on the regions of contact both viruses may conversely infect either the oral or genital mucosa. These viruses have the capacity to invade and replicate in the central nervous system and establish a latent infection in dorsal root ganglia. Diseases caused by HSV may become life threatening in immunocompromised patients, especially human immunodeficiency virus (HIV) infected patients. After primary infection, HSV persists in the host for the latter's entire lifetime, thus HSV infection is considered as a lifelong infection (The Journal of Infectious Diseases, 2002, 186, S71-S77).

Several antivirals that are being used for treating herpes include acyclovir, valacyclovir, famciclovir and penciclovir. Among the listed antiviral agents, acyclovir is used for the treatment of viral infections caused by HSV-1 and HSV-2.

*Ficus arnottiana*, widely distributed in India and Sri Lanka, is medium sized deciduous tree without aerial roots. The plant is useful against skin diseases, inflammation, diarrhea, diabetes, burning sensation, leprosy, scabies, and wounds as per the traditional Ayurvedic System of Medicine (Natural Product Radiance, 2009, 8 (5), 478-482).

There continues to be a need for effective compositions and methods for the prevention and treatment of viral infections, particularly herpes infections. The incidence and severity of herpes infections have increased due to increase in the number of immunocompromised patients produced by aggressive chemotherapy regimens, expanded organ transplantation and the rising incidence of HIV infections.

To our knowledge, there is no report of any medicament containing extract of the plant *Ficus arnottiana* for treatment of viral infections.

SUMMARY OF THE INVENTION

The present invention relates to a composition comprising a therapeutically effective amount of an isolated extract of the plant *Ficus arnottiana* in combination with a pharmaceutically acceptable carrier.

The invention also relates to a process for the preparation of the extract of the plant *Ficus arnottiana* and the composition containing the isolated extract as the active ingredient.

The invention also relates to the antiviral activity of the composition.

In an aspect of the invention, the antiviral activity of the composition is anti-HSV activity. In an aspect, the invention relates to a composition comprising a therapeutically effective amount of an isolated extract of the plant *Ficus arnottiana* and a pharmaceutically acceptable carrier; for use in the prevention and treatment of a viral infection caused by herpes simplex virus (HSV).

The invention further relates to a method of treating a viral infection caused by herpes simplex virus (HSV) in a subject comprising administering to the subject a composition comprising a therapeutically effective amount of an isolated extract of the plant *Ficus arnottiana* in combination with a pharmaceutically acceptable carrier.

The invention also relates to the composition comprising a therapeutically effective amount of an isolated extract of the plant *Ficus arnottiana* and a pharmaceutically acceptable carrier for use in the prevention of viral infection with the use of condoms or other barrier devices.

The invention includes the composition comprising a therapeutically effective amount of an isolated extract of the plant *Ficus arnottiana* in combination with a pharmaceutically acceptable carrier for use in the prevention and treatment of viral infections caused by herpes simplex virus (HSV).

The invention also includes the use of the isolated extract of the plant *Ficus arnottiana* for the manufacture of a medicament for the treatment of viral infection caused by herpes simplex virus (HSV).

DETAILED DESCRIPTION OF THE INVENTION

Before describing the present invention in detail, it has to be understood that this invention is not limited to particular embodiments. It is also to be understood that the terminology used herein is for the purpose of describing particular embodiments only, and is not intended to be limiting.

As used in the specification and claims, the singular forms "a", "an" and "the" include plural references unless the context clearly indicates otherwise.

Unless defined otherwise, all technical and scientific terms used herein have the same meaning as commonly understood by one of the ordinary skill in the art to which the invention belongs.

The term "treating", "treat" or "treatment" as used herein includes preventive (prophylactic) and palliative treatment.

The term "*Ficus arnottiana*" also includes the synonyms such as "*Ficus populifolia*", "*Urostigma arnottianum*" or "*Urostigma cordifolium*".

"Extract" or "isolated extract" mentioned herein means a blend of compounds present in the plant or fractions obtained from the plant *Ficus arnottiana*. Such compounds or fractions are obtained by extraction of ground whole plant or parts of the plant *Ficus arnottiana* such as stem (stem with bark), stem without bark, bark and twigs using appropriate solvents and the step of extraction is optionally followed by further enrichment. The terms "extract" and "isolated extract" may be used interchangeably.

"Antiviral drugs" mentioned herein refers to a class of therapeutic agents used specifically for treating viral infections, particularly those caused by herpes simplex viruses such as herpes simplex virus type 1 (HSV-1), herpes simplex virus type 2 (HSV-2), cytomegalovirus (CMV), Epstein-Barr virus (EBV), varicella zoster virus (VZV), and human herpes viruses 6, 7 and 8 (HHV-6, HHV-7 and HHV-8) and the like.

"Composition" mentioned herein refers to an herbal composition or a pharmaceutical composition comprising a therapeutically effective amount of an extract or the isolated extract of the plant *Ficus arnottiana* in combination with a pharmaceutically acceptable carrier. It should be noted that the term "composition" should be construed in a broad sense and includes any composition which is intended for the purpose of achieving a therapeutic effect whether sold as a pharmaceutical product, for example carrying a label as to the intended indication, whether sold over the counter, or whether sold as a phytopharmaceutical.

As used herein, the term "therapeutically effective amount" means an amount of the extract of the plant *Ficus arnottiana* that yields a desired therapeutic response such as, alleviating, treating and/or preventing the viral infection or the symptoms of skin lesions, sores, cold sores, blisters, warts, lumps, bumps, pimples, rashes and ulcers associated with or caused by a viral infection, particularly caused by HSV-1 or HSV-2.

By "pharmaceutically acceptable" it is meant the carrier, diluent, excipients, and/or salt must be compatible with the other ingredients contained in the formulation, and not deleterious to the recipient thereof.

As used herein, the term "pharmaceutically acceptable carrier" means a non-toxic, inert solid, semi-solid, diluent such as water, encapsulating material or formulation auxiliary of any type. Some non-limiting examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate; as well as coloring agents; releasing agents; coating agents; sweetening, flavoring and perfuming agents; preservatives such as phenolip, methyl paraben, butyl paraben and propyl paraben; antioxidants; oils or waxes such as beeswax, carnauba wax, hard wax, yellow wax and cetyl esters; emulsifiers such as glyceryl monostearate; petrolatums such as paraffin, lanolin alcohols, white petrolatum, yellow petrolatum, wool alcohols, petroleum jelly and petroleum wax; glycols such as propylene glycol, methyl glycol and methyl ethylene glycol; carbomers such as carpopol 974P; poly oxy ethylene alkyl ethers such as cetosteryl alcohol; plasticizers such as triethanolamine; solvents and hydrophilic gelling agents can also be present in the composition, according to the judgment of the formulator.

The term "bioactive marker" used herein refers to biologically active chemical compounds which are present in the extract of the whole plant or parts of the plant *Ficus arnottiana* such as stem (stem with bark), stem without bark, bark and twigs. The bioactive markers isolated from the extract of the stem of the plant *Ficus arnottiana* exhibit antiviral activity.

The term "subject" as used herein refers to an animal, particularly a mammal, and more particularly a human. The term "mammal" used herein refers to warm-blooded vertebrate animals of the class Mammalian, including humans, characterized by a covering of hair on the skin and, in the female, milk-producing mammary glands for nourishing the young. The term mammal includes animals such as cat, dog, rabbit, bear, fox, wolf, monkey, deer, mouse, pig and the human.

The plant, *Ficus arnottiana* is a commonly distributed species in India and Sri Lanka. The whole plant of the species or parts of the plant such as stem, stem without bark, bark and twigs were collected from various locations in and around Maharashtra, India such as Belgaum, Kolhapur, Goa. The freshly collected plants or parts of the plant were dried. For taxonomic characterization, herbarium specimens in flowering and fruiting were collected and deposited in the departmental herbarium of Piramal Healthcare Limited (Formerly Piramal Life Sciences Limited), Goregaon, Mumbai, India. Based on morphological characters, the herbarium specimen was identified as *Ficus arnottiana*. The extracts obtained and used in this invention are not limited to those obtained from *Ficus arnottiana* plants grown in Maharashtra, India and the extract may be obtained from any *Ficus arnottiana* plant grown in other regions.

The present invention relates to an isolated extract from the whole plant or one or more parts of the plant *Ficus arnottiana* prepared by stirring ground whole plant or one or more parts of the plant in a solvent; followed by concentrating the resulting extract; and optionally enriching the extract by solvent partitioning. Plant parts that can be used include stem with bark, stem without bark, bark, leaves, twigs, roots, flowers, inflorescence, seeds and fruits. It is preferred that the plant parts used are selected from stem (stem with bark), stem without bark, bark and twigs.

The present invention further relates to a composition comprising a therapeutically effective amount of an isolated extract of the whole plant or one or more parts of the plant, *Ficus arnottiana* in combination with a pharmaceutically acceptable carrier.

The invention also relates to a process for the preparation of the extract of the plant *Ficus arnottiana* and the composition containing the extract as the active ingredient.

The process for the preparation of the composition includes the following steps:
(a) preparing an extract from the ground whole plant or one or more parts of the plant *Ficus arnottiana* by stirring in a solvent in a ratio of 1:8 to 1:10 weight/volume for 3 hours to 12 hours at 30° C. to 50° C.;
(b) concentrating the extract obtained in step (a);
(c) optionally drying the extract obtained in step (b) under high vacuum (0.01-5 mm Hg);
(d) optionally enriching the extract obtained in step (b) or step (c) by solvent partitioning; and
(e) mixing the extract obtained in step (b), step (c) or step (d) with a pharmaceutically acceptable carrier to obtain the composition.

In an aspect of the invention the extract obtained in step (b), step (c) or step (d) may be used without a pharmaceutically acceptable carrier.

In another aspect of the invention the plant parts are selected from stems, bark, stems without bark and twigs.

In an embodiment, the composition of the present invention comprises extract of the stem of the plant *Ficus arnottiana*. Accordingly, there is provided a process for the preparation of the composition comprising extract of the stem of the plant *Ficus arnottiana* and includes the following steps:
(a) preparing an extract from the stem of the plant *Ficus arnottiana* by stirring in a solvent in a ratio of 1:8 to 1:10 weight/volume for 3 hours to 12 hours at 30° C. to 50° C.;
(b) concentrating the extract obtained in step (a);
(c) optionally drying the extract obtained in step (b) under high vacuum (0.01-5 mm Hg);
(d) optionally enriching the extract obtained in step (b) or step (c) by solvent partitioning; and
(e) mixing the extract obtained in step (b), step (c) or step (d) with a pharmaceutically acceptable carrier and formulating into therapeutic dosage forms.

In an aspect of the invention the extract obtained in step (b), step (c) or step (d) may be used without a pharmaceutically acceptable carrier.

The whole plant or one or more parts of the plant *Ficus arnottiana* may be ground and the whole plant or one or more parts of the plant *Ficus arnottiana* may be coarsely ground or ground to a powder or ground to another type of texture.

In an embodiment of the invention, the solvent for extracting ground whole plant or one or more parts of the plant *Ficus arnottiana* is selected from methanol, ethanol, n-propanol, isopropanol, n-butanol, acetone, ethyl acetate, dichloromethane, water, or mixtures thereof, preferably mixture of methanol and water.

In an embodiment of the invention, the solvent extract is filtered before concentration.

In an embodiment of the invention, concentration of the solvent extract is done by using one or more of the methods selected from (i) distillation under reduced pressure (150-600 mm Hg) at 30° C. to 50° C.; (ii) lyophilization; and (iii) spray drying to obtain the extract.

In an embodiment of the invention, the solvents for enriching the extract by solvent partitioning are selected from water, petroleum ether, dichloromethane, chloroform, ethyl acetate, methanol, acetone, acetonitrile, n-propanol, iso-propanol, and butanol or mixtures thereof.

In an aspect of the invention, one or more bioactive markers are isolated from the extract of the whole plant or one or more parts of the plant *Ficus arnottiana*.

In an embodiment of the invention, two bioactive markers are identified in the extract of the plant *Ficus arnottiana*. The bioactive markers are isolated from the extract and are specifically identified as phlorizin and 5,7,4'-trihydroxyflavone.

In another embodiment of the invention, two bioactive markers are isolated from the composition comprising the extract of the plant *Ficus arnottiana*. The bioactive markers are identified as phlorizin and 5,7,4'-trihydroxyflavone.

Accordingly, in one aspect, the present invention relates to a composition comprising a therapeutically effective amount of the extract of the plant *Ficus arnottiana* containing one or more bioactive markers for use in the prevention and treatment of a viral infection caused by herpes simplex virus (HSV).

In one embodiment, the bioactive marker contained in the extract is phlorizin and 5,7,4'-trihydroxyflavone or a mixture thereof.

In an embodiment, the present invention relates to the bioactive marker(s) isolated from the extract of the plant *Ficus arnottiana* for use in the treatment of a viral infection caused by herpes simplex virus (HSV), wherein the HSV may be HSV-1 or HSV-2; and wherein the bioactive marker is selected from phlorizin or 5,7,4'-trihydroxyflavone or mixtures thereof.

The present invention further relates to a method of treating a viral infection caused by herpes simplex virus (HSV) in a subject, which comprises administering to the subject the composition comprising a therapeutically effective amount of the isolated extract of the plant *Ficus arnottiana*.

The present invention still further relates to a method of treating a viral infection caused by HSV in a subject, wherein the HSV is HSV-1, which comprises administering to the subject the composition comprising a therapeutically effective amount of the isolated extract of the plant *Ficus arnottiana*.

The present invention also relates to a method of treating viral infection caused by HSV in a subject, wherein the HSV is HSV-2, which comprises administering to the subject the composition comprising a therapeutically effective amount of the isolated extract of the plant *Ficus arnottiana*.

The present invention also relates to the composition comprising a therapeutically effective amount of an isolated extract of the plant *Ficus arnottiana* in combination with a pharmaceutically acceptable carrier for use in the prevention and treatment of viral infection caused by HSV.

The present invention further relates to the composition comprising a therapeutically effective amount of an isolated extract of the plant *Ficus arnottiana* in combination with a pharmaceutically acceptable carrier for use in the prevention and treatment of viral infection caused by HSV, wherein the HSV is HSV-1.

The present invention still further relates to the composition comprising a therapeutically effective amount of an isolated extract of the plant *Ficus arnottiana* in combination with a pharmaceutically acceptable carrier for use in the prevention and treatment of viral infection caused by HSV, wherein the HSV is HSV-2.

The present invention also relates to the use of a therapeutically effective amount of an isolated extract of the plant *Ficus arnottiana* in combination with a pharmaceutically acceptable carrier for the manufacture of a medicament for the treatment of viral infection.

In an aspect of the invention, the subject to be treated or the subject to which the use is directed to, is a mammal, particularly a human who has been diagnosed as having an infection caused by a virus. More particularly, the mammal to be treated is a human who has been diagnosed as having an infection caused by a HSV.

In another aspect of the invention, the subject to be treated is a mammal, particularly a human who has been diagnosed as being infected with human immunodeficiency virus (HIV) to whom the composition is administered as a prophylactic measure against co-infection with HSV-1.

In yet another aspect of the invention, the subject to be treated is a mammal, particularly a human who has been diagnosed as being infected with human immunodeficiency virus (HIV) to whom the composition is administered as a prophylactic measure against co-infection with HSV-2.

In a further aspect of the invention, the mammal to be treated is a human to whom the composition is administered as a prophylactic measure against sexually transmitted infection (STI).

In another aspect of the invention, the subject to be treated is a mammal, particularly a human who has been diagnosed as having recurrent infections caused by a HSV.

The present invention also envisages the use of the composition of the present invention in combination with other antiviral drugs such as acyclovir, famciclovir, ganciclovir, imunovir, indinavir or oseltamivir.

In an aspect of the invention, the method of treating viral infection includes the administration of the composition described above, by known routes of administration, etc. including the following:

The composition can be administered orally, for example in the form of pills, tablets, coated tablets, capsules, granules, solutions, elixirs or syrup.

According to the present invention, the composition formulated for oral administration (oral formulations) contains about 5% to about 99% by weight of the extract of the plant *Ficus arnottiana*. The oral formulation is prepared by thoroughly blending the extract of the plant *Ficus arnottiana* into a conventional base such as sugars, starches or lubricants.

The composition can be used for topical or transdermal administration. The topical compositions of the present invention include formulations suitable for topical or transdermal application to skin, suitable for administration to mucous membranes, or administration in conjunction with a condom or other barrier device. The compositions can be formulated into a wide variety of product types that include but are not limited to lotions, creams, gels, sticks, patches, vaginal suppositories or pessaries, sprays or ointments.

According to the present invention, the composition formulated for topical or transdermal application contains about 5% to about 99%, preferably 5 to 50%, by weight of the extract of the plant *Ficus arnottiana*. The topical or transdermal formulation is prepared by blending the extract of the plant *Ficus arnottiana* into a conventional base such as oils, waxes or glycols.

The extract of the plant *Ficus arnottiana* is contained in the composition of the present invention in such an amount which is effective to achieve the desired therapeutic response for a particular patient without being toxic to the patient or causing severe side effects. The effective amount will depend upon a variety of factors including the potency of the extract of the present invention employed, the route of administration, the time of administration, the rate of excretion of the particular composition being employed, the duration of the treatment, the age, sex, weight, condition, general health and prior medical history of the patient being treated, and like factors well known in the medical arts.

The efficacy of the extract of the plant *Ficus arnottiana* has been established by biological assays which are described in detail in the following examples. These examples are herein provided for the purpose of illustration only and are not intended to limit the scope of the invention.

EXAMPLES

[Note: The water used in the experimental protocols is demineralized water.]

Example 1

Preparation of Dichloromethane (DCM) and Methanol (1:1) Extract of *Ficus arnottiana*

The freshly collected stem of *Ficus arnottiana* was dried using dehumidifier and pulverized. The coarsely ground material (150 g) was soaked in 1500 mL DCM: methanol (1:1), with constant stirring, for 3 hours in a round bottom flask that was placed in the water bath maintained at 40° C.±5° C. The extract was filtered and the residue was soaked in 1500 mL DCM:methanol (1:1) for 3 hours at 40° C.±5° C. and filtered. The extracts were combined and concentrated using rotary evaporator at 45° C. under line vacuum (about 500 mm Hg) to obtain 5.0 g of crude extract (designated as Sample 1).

Extracts of other plant parts such as stem bark, stem without bark and twig using DCM:methanol (1:1) were prepared by following the same procedure as that used for the stem. The yields of the extracts are as follows:

(i) 2.5 g of extract was obtained from 50 g of bark (designated as Sample 2).
(ii) 2.0 g of extract was obtained from 50 g of stem without bark (designated as Sample 3).
(iii) 16.3 g of extract was obtained from 300 g of twig (designated as Sample 4).

Example 2

Enrichment of the Sample 1, Sample 2, Sample 3 and Sample 4 of Example 1

Step 1. Sample 1 (1 g) was suspended in 30 mL of water:methanol (9:1) at room temperature (25° C.±5° C.) and sonicated to dissolve and partitioned 3 times successively with 30 mL petroleum ether (60° C.-80° C.). The petroleum ether layer was concentrated on rotary evaporator under line vacuum to obtain 0.5 g petroleum ether fraction (designated as Sample 5).

Step 2. The aqueous filtrate obtained from step 1 was partitioned 3 times successively with 30 mL chloroform. The chloroform layer was concentrated on rotary evaporator under line vacuum to obtain 0.10 g chloroform fraction (designated as Sample 6).

Step 3. The aqueous layer obtained from the step 2 was then partitioned 3 times successively with 30 mL ethyl acetate. The ethyl acetate layer was concentrated in rotary evaporator under line vacuum to obtain 0.07 g ethyl acetate fraction (designated as Sample 7).

Step 4. The aqueous layer obtained from step 3 was then concentrated in rotary evaporator under line vacuum to remove residual organic solvents and lyophilized to obtain 0.24 g aqueous fraction (designated as Sample 8).

Enrichment of extracts of other plant parts such as stem bark, stem without bark and twig was performed in the same manner as for extract of the stem. The yields of the extracts are as follows:

(i) 1 g of Sample 2 was enriched to obtain 0.06 g petroleum ether fraction (designated as Sample 9); 0.16 g chloroform fraction (designated as Sample 10); 0.07 g ethyl acetate fraction (designated as Sample 11) and 0.24 g aqueous fraction (designated as Sample 12).

(ii) 1 g of Sample 3 was enriched to obtain 0.21 g petroleum ether fraction (designated as Sample 13); 0.19 g chloroform fraction (designated as Sample 14); 0.29 g ethyl acetate fraction (designated as Sample 15) and 0.28 g aqueous fraction (designated as Sample 16).

(iii) 1 g of Sample 4 was enriched to obtain 0.64 g petroleum ether fraction (designated as Sample 17); 0.15 g chloroform fraction (designated as Sample 18); 0.03 g ethyl acetate fraction (designated as Sample 19) and 0.08 g aqueous fraction (designated as Sample 20).

Example 3

Preparation of Methanol Extract of the Plant, *Ficus arnottiana*

The freshly collected stem of *Ficus arnottiana* was dried and pulverized. The coarsely ground material (50 g) was soaked in 500 mL methanol with stirring, for 3 hours in a round bottom flask that was placed in the water bath maintained at 40° C.±5° C. The extract was filtered and the residue was soaked in 500 mL methanol for 3 hours at 40° C.±5° C. and filtered. The extracts were combined and concentrated using rotary evaporator under line vacuum to obtain 2.06 g of extract (designated as Sample 21).

Methanol extract of twig of the plant *Ficus arnottiana* was prepared by following the same procedure as that used for the stem. 3.95 g of extract (designated as Sample 22) was obtained from 50 g of twig.

Example 4

Preparation of Methanol:Water (1:1) Extract of the Plant, *Ficus arnottiana*

The freshly collected stem of *Ficus arnottiana* was dried and pulverized. The coarsely ground material (100 g) was soaked in 1 L methanol:water (1:1) with constant stirring, for 3 hours in a round bottom flask that was placed in the water bath maintained at 40° C.±5° C. The extract was filtered and the residue was soaked in 800 mL methanol:water (1:1) for 3 hours at 40° C.±5° C. and filtered. The extracts were combined and concentrated using rotary evaporator under line vacuum and lyophilized to obtain 5.67 g of hydromethanolic extract (designated as Sample 23).

Hydromethanolic extract of twig of the plant *Ficus arnottiana* was prepared by following the same procedure as that used for the stem. 4.03 g of extract (designated as Sample 24) was obtained from 50 g of twig.

Example 5

Preparation of Water Extract of the Plant, *Ficus arnottiana*

The freshly collected stem of *Ficus arnottiana* was dried and pulverized. The coarsely ground material (50 g) was soaked in 500 mL water, with constant stirring, for 3 hours in a round bottom flask that was placed in the water bath maintained at 45° C.±5° C. The extract was filtered and lyophilized to obtain 1.04 g of extract (designated as Sample 25).

Water extract of twig of the plant *Ficus arnottiana* was prepared by following the same procedure as that used for the stem. 1.11 g of extract (designated as Sample 26) was obtained from 50 g of twig.

Example 6

Preparation of Formulation

General Procedure for the Preparation of Cream.

Dissolved required amount of methyl paraben and propyl paraben in propylene glycol and water (refer to Table 1) in a suitable glass/stainless steel vessel with slight heating. Sample 23 of Example 4 was added to the vessel and dissolved/dispersed using mechanical stirrer. The temperature was maintained at 60° C. to 75° C. Glyceryl monostearate and propylene glycol were added to this solution under constant stirring. Beeswax, white soft paraffin and glyceryl monostearate were melted and added to the above vessel under constant stirring. The temperature was reduced slowly to room temperature.

TABLE 1

Formulation IA, Formulation IB and Formulation IC

| No. | Ingredients | Formulation IA % w/w | Formulation IB % w/w | Formulation IC % w/w |
|---|---|---|---|---|
| 1 | Sample 23 of Example 4 | 10 | 20 | 30 |
| 2 | Beeswax | 2 | 2 | 2 |
| 3 | White soft paraffin | 76.8 | 61.8 | 46.8 |
| 4 | Glyceryl monostearate | 3 | 3 | 3 |
| 5 | Propylene glycol | 3 | 3 | 3 |
| 6 | Methyl paraben | 0.18 | 0.18 | 0.18 |
| 7 | Propyl paraben | 0.02 | 0.02 | 0.02 |
| 8 | Water | 5 | 10 | 15 |
| | Total | 100 | 100 | 100 |

Example 7

Analytical Analysis

Part A: Evaluation of Sample 23 of Example 4.

Dissolved 100 mg of the sample 23 of Example 4 in 1 mL of methanol:water (1:1); treated with 1 mL of 0.04 M KMnO4 and stored for 15 minutes at room temperature.

The mixture was diluted with diluent [methanol:water (1:1)] and filtered through 0.45μ polyvinylidene fluoride (PVDF) filter and filtrate analyzed by HPLC.

Figure 1:
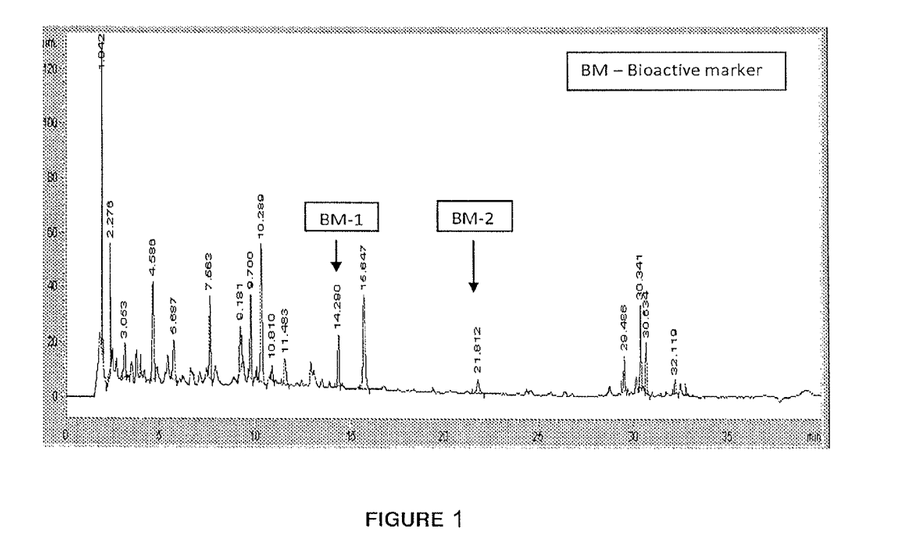
FIG. 1 shows chromatogram of sample 23 of Example 4 analyzed by HPLC. The chromatogram shows two bioactive marker (BM) peaks namely BM-1 and BM-2.

Analytical HPLC conditions:
Column: Unisphere aqua C18, 150×4.6 mm, 3 μm
Mobile phase A: 0.1% trifluoroacetic acid
Mobile phase B: acetonitrile
Gradient: time (minutes)/% A: 0/90, 25/60, 30/20, 35/20, 36/90, 40/90
Run time: 40 minutes
Concentration: 10 mg/mL
Diluent: methanol:water (1:1)
Wavelength: 270 nm
Result:

FIG. 1 depicts an analytical chromatogram of sample 23 of Example 4. The chromatogram illustrates two bioactive marker peaks, designated as BM 1 (bioactive marker 1) and BM 2 (bioactive marker 2), at retention time of 14.3 and 21.8 respectively. The bioactive markers exhibited antiviral activity. BM 1 and BM 2 were isolated and purified as described in Part C.

Part B: Evaluation of Formulation IB of Example 6.

Dissolved 1 g of Formulation IB of Example 6 in 15 mL of methanol:water (1:1) and heated at 60° C. for 20 minutes. The resulting solution was diluted with the diluent up to 20 mL and filtered through 0.45μ polyvinylidene fluoride (PVDF) filter and the filtrate was analyzed by HPLC.

Figure 2:
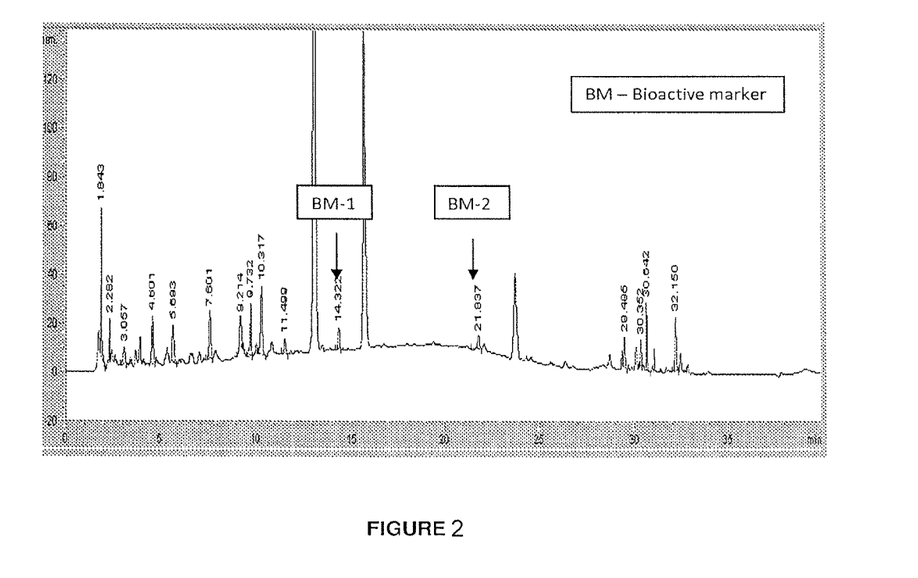
FIG. 2 shows chromatogram of Formulation IB of Example 6 analyzed by HPLC. The chromatogram shows two bioactive marker (BM) peaks namely BM-1 and BM-2.

Analytical HPLC conditions:
Column: Unisphere aqua C18, 150×4.6 mm, 3 μm
Mobile phase A: 0.1% trifluoroacetic acid
Mobile phase B: acetonitrile
Gradient: time (minutes)/% A: 0/90, 25/60, 30/20, 35/20, 36/90, 40/90
Run time: 40 minutes
Concentration: 50 mg/mL
Diluent: methanol:water (1:1)
Wavelength: 270 nm
Result:

FIG. 2 depicts an analytical chromatogram of Formulation IB of Example 6. The chromatogram illustrates two bioactive marker peaks, designated as BM 1 and BM 2, at retention time of 14.3 and 21.8 respectively. The bioactive markers exhibited antiviral activity. BM 1 and BM 2 were isolated and purified as described in Part C.

Part C: Isolation of Bioactive Markers.

85.0 g of sample 23 of Example 4 was dissolved in 1.6 L of methanol; sonicated for 10 minutes and was allowed to settle for 30 minutes. Supernatant was decanted and filtered to obtain filtrate no. 1. The insoluble portion was washed with 200 mL methanol. The supernatant was filtered to obtain filtrate no. 2. The filtrates no. 1 and 2 were pooled and dried on rotavapour to obtain 26.18 g of sample. 13.0 g of the resulting sample was dissolved in 36 mL of methanol:water (75:25; v:v), sonicated, centrifuged. The supernatant was loaded on LH-20 column (5×80 cm) and elution was done with methanol:water (75:25; v:v). Another batch of 13.0 g of sample was processed in the procedure described above. The fractions were collected and analyzed by HPLC.

Analytical HPLC conditions:
Column: Unisphere C18, 250×4.6 mm, 5 μm
Mobile phase A: 0.1% trifluoroacetic acid
Mobile phase B: acetonitrile
Gradient: time (minutes)/% A: 0/90, 30/20, 35/20, 36/90, 40/90
Run time: 40 minutes
Injection volume: 10 μL
Wavelength: 270 nm The fractions from the two LH-20 columns were pooled and concentrated to dryness at 40° C. under vacuum to obtain 100 mg of bioactive marker 1 and 135 mg bioactive marker 2. The dried samples of bioactive markers 1 and 2 were separately subjected to C-18 flash chromatography for further purification.

Chromatographic conditions for flash chromatography:
Column: Redisep C18, 14×2 cm
Mobile phase A: 0.1% trifluoroacetic acid
Mobile phase B: acetonitrile
Gradient: time (minutes)/% A: 0/90, 30/20, 35/20, 36/90, 40/90
Flow: 30 mL/minute
Wavelength: 270 nm Bioactive Marker 1:

The fractions of flash chromatography were monitored by HPLC. The fractions containing bioactive marker 1 were pooled and evaporated at 40° C. under vacuum to dryness to obtain 30 mg of semipure bioactive marker 1 which was further purified using silica semi-preparative HPLC to obtain 5.3 mg of bioactive marker 1. Bioactive marker 1 is present in the sample 23 of Example 4 in the range of 0.02 to 0.8%.

Chromatographic conditions for silica semi-preparative HPLC:
Column: Grace silica, 5μ (250×10 mm)
Mobile phase: methanol:dichloromethane (10:90); v:v
Flow: 5 mL/minute
Wavelength: 270 nm
Sample conc.: 20 mg/mL Based on the Mass and NMR data, the bioactive marker 1 was identified as phlorizin. Molecular formula of phlorizin is $C_{21}H_{24}O_{10}$ and molecular weight is 436.41.

Bioactive Marker 2:

The fractions of flash chromatography were monitored by HPLC. Crystals of bioactive marker 2 were obtained from the fractions. The crystals were separated by decantation and dried to obtain 20 mg of bioactive marker 2. Based on Mass and NMR data, the bioactive marker 2 was identified as 5,7,4'-trihydroxyflavone. Molecular formula of 5,7,4'-trihydroxyflavone is $C_{15}H_{10}O_5$ and molecular weight is 270.05. Bioactive marker 2 is present in the sample 23 of Example 4 in the range of 0.01 to 0.1%.

Biological Evaluation

In Vitro Antiviral Assays

Example 8

Preparation of Viral Stock

Materials used:
Cell line: Vero (Kidney epithelial cells of African green monkey kidney cell line-American Type Culture Collection (ATCC) #CCL-81)
Virus: HSV-1 (ATCC strain VR-1493 and clinical strain from National Institute of Virology, Pune, India): HSV-2 (ATCC strain VR-734 and clinical strain from National Institute of Virology, Pune, India)
Medium: Dulbecco's Modified Eagle Medium (DMEM, Gibco, USA, Cat no: 12430)
Serum: Fetal Bovine Serum (FBS, Gibco, USA, Cat no: 16000-044)
Trypsin-EDTA solution: 0.25% Trypsin-Ethylenediaminetetra-aceticacid (Trypsin-EDTA, Gibco, USA, Cat no: 25200)
Standard compound: Acyclovir (Medicorp, Hyderabad, India)

Plasticwares: Tissue culture flasks 25 cm² (Nunc, USA, Cat no: 156367): Tissue culture flasks 75 cm² (Nunc, USA, Cat no: 156499): Centrifuge tubes 15 mL (Nunc, USA, Cat no: 366060): Centrifuge tubes 50 mL (Nunc, USA, Cat no: 373687): Flat bottom 96-well plates (Nunc, USA, Cat no: 167008)

Stain: Crystal violet (Sigma, USA, Cat no: C3886-25G)

Antibiotic-antimycotic: (Gibco, USA, Cat no: 15240) mixture 3-(4,5-dimethylthiazol-2-yl)-2,5-diphenyl tetrazolium bromide (MTT) reagent: (Trevigen Inc, Gaithersburg Md., Cat no. 4890-25-01)

Detergent Reagent: (Trevigen Inc, Gaithersburg Md., Cat no: 4890-25-02)

Step 1

Maintenance of the Cell Line.

Maintenance of the cell line was performed as reported in Antiviral Research, 2005, 67, 24-30 incorporated herein by reference for its procedure.

Vero cell line obtained from ATCC was propagated in complete growth medium i.e. Dulbecco's Modified Eagle Medium (DMEM) supplemented with 10% Fetal Bovine Serum (FBS) and 1× antibiotic-antimycotic mixture. T-25 tissue culture flask with cell monolayer was selected for subculturing. DMEM from the flask was removed and briefly rinsed with DMEM without serum to remove all traces of serum that contains trypsin inhibitor. 1 mL of Trypsin-EDTA solution was added to flask and observed under an inverted microscope until cell monolayer was dispersed (usually within 3-5 minutes). Immediately, 14 mL of complete growth medium was added and cells were aspirated by gentle pipetting. A subcultivation ratio of 1:3 was obtained by adding each 5 mL of cell suspension to 3 different T-25 tissue culture flasks. Flasks were maintained at 37° C. with 5% $CO_2$.

Step 2

Virus (HSV-1 and HSV-2) Propagation.

Virus propagation was performed as reported in Antiviral Research, 2005, 67, 24-30 incorporated herein by reference for its procedure.

HSV-1 and HSV-2 were propagated in Vero cells. Briefly, Vero cells were grown in DMEM supplemented with 10% FBS, penicillin and streptomycin (complete medium) at 37° C. with 5% $CO_2$. When cells attained 80-90% confluence, the monolayer obtained was washed with plain DMEM and infected with appropriate dilutions of virus. Virus was allowed to adsorb to monolayer for 1 hour at 37° C. with 5% $CO_2$. After one hour, virus inoculum was removed and 10 mL of DMEM supplemented with 2% FBS was added and flask was incubated further for 48 hours till the complete disruption of cell monolayer. Flask was observed microscopically twice daily for cytopathic effect (CPE). CPE are alterations in cellular morphology, such as rounding and enlargement of cells, synctia and inclusion formation, caused by the virus. After 48 hours of incubation, flask was then subjected to 2-3 freeze thaw cycles for complete cell lysis and release of the virus into the culture medium. Cell debris was removed by centrifugation at 1000 rpm, for 10 minutes at 4° C. The supernatant obtained was stored as aliquots at −80° C. Titer of the viral stock was determined using following methods:

Step 3(A)

Determination of Viral Titer Using Cytopathic Effect (CPE) Assay.

The assay was done as reported in World J. Gastroenterol., 2006, 12: 4078-4081 incorporated herein by reference for its procedure.

Viral titer was determined by CPE assay and was expressed as tissue culture infectious dose 50 ($TCID_{50}$). Vero cells (obtained in step 1) were seeded in 96-well plate at a density of $2 \times 10^4$ cells/100 μL/well and then incubated at 37° C. with 5% $CO_2$ for 24 hours for 80-90% confluency. A serial dilution of viral stock (obtained in step 2) was carried out ($10^{-1}$ to $10^{-8}$) in maintenance medium (DMEM with 2% FBS). Growth medium from the culture plate was removed and 100 μL of each dilution of virus was used for infecting Vero cells. Vero cells only with maintenance medium served as cell control. Post infection, the culture plate was incubated at 37° C. in a $CO_2$ incubator for 48 hours. After 48 hours of incubation, the CPE was examined under an inverted microscope in the wells inoculated with virus dilutions. When virus controls showed the maximum CPE, media was removed and the infected monolayer was fixed and stained using a solution containing formalin (10%) and crystal violet (1%) for 30 minutes. At the end of 30 minutes, the stain was aspirated out and the plate rinsed using distilled water until all excess stain was washed away. The plate was allowed to dry overnight. The viral titer ($TCID_{50}$) was calculated as described in Am. J. Hyg., 1938, 27, 493-497. $TCID_{50}$ represents the dose that gives rise to CPE in 50% of inoculated cultures.

Result: Viral titer of HSV-1 determined by CPE Assay was $5.88 \times 10^6$ $TCID_{50}$/mL. Viral titer of HSV-2 determined by CPE Assay was $1.58 \times 10^7$ $TCID_{50}$/mL.

Step 3(B)

Determination of Viral Titer Using Plaque Assay.

The assay was done as reported in Antiviral Res., 2005, 67(1): 24-30 incorporated herein by reference for its procedure.

Viral titer was also determined by plaque assay and was expressed as plaque forming units per mL (pfu/mL). Vero cells (obtained in step 1) were trypsinized, counted and plated into 24-well plate at a density of $2 \times 10^5$ cells/mL/well and incubated at 37° C. with 5% $CO_2$ for 24 hours for 80-90% confluency. Serial dilutions of virus (from viral stock obtained in step 2) were prepared in the range of $10^{-2}$ to $10^{-7}$ using maintenance medium (DMEM with 2% FBS). Growth medium from the plate was removed and 0.2 mL of each dilution of virus was added to each well taking care not to dislodge any cells. Infected monolayers were incubated at 37° C. with 5% $CO_2$ for 1 hour with shaking every 15 minutes. After the incubation period, 1% CMC was added to each well in 1 mL volume and plate was incubated for 48 hours, after which the cells were fixed and stained with a solution containing formalin (10%) and crystal violet (1%) for 30 minutes. At the end of 30 minutes, the stain was aspirated out and the plate was rinsed using distilled water until all excess stain was washed away. The plates were allowed to dry overnight. Plaques were counted to estimate the viral titer which is expressed as plaque forming units per mL (pfu/mL).

Viral titer=(No. of plaques produced×dilution of virus× vol. of inoculum)

Result: Viral titer of HSV-1 determined by the plaque assay was $2.1 \times 10^8$ pfu/mL. Viral titer of HSV-2 determined by the plaque assay was $1.65 \times 10^7$ pfu/mL.

Example 9

Primary Antiviral Screening Test was Performed Using CPE Inhibition Assay (Crystal Violet Staining Method)

The assay was designed to detect agents (in this case, the extracts) exhibiting activity at any stage of the virus reproductive cycle. The assay was done as reported in Indian J. Med. Res., 2004, 120:24-29 incorporated herein by reference for its procedure.

Vero cells (obtained in step 1 of Example 8) were propagated at a density of $1 \times 10^4$ cells/well in 96 well plate and incubated at 37° C. in a $CO_2$ incubator for 24 hours to form a monolayer. Samples 1 to 26 were tested by adding at 50 µg/mL and 100 µg/mL concentration (DMSO stock of 20 mg/mL of the extract was diluted to 50 µg/mL and 100 µg/mL with DMEM containing 2% FBS) in a final culture volume of 200 µL/well. Appropriate controls were included such as Vero cells alone (cell control), Vero cells with virus (virus control) and Vero cells with virus and the standard compound, acyclovir (a commercially available antiviral drug). Acyclovir was tested at the following concentrations (DMSO stock of 20 mg/mL of acyclovir was diluted to 100 µg/mL with DMEM containing 2% FBS): 12.5 µg/mL, 6.25 µg/mL, 3.125 µg/mL, 1.5 µg/mL and 0.78 µg/mL against HSV-1 and 25 µg/mL, 12.5 µg/mL, 6.25 µg/mL and 3.125 µg/mL against HSV-2. The extracts to be assayed were added 1 hour prior to infection to provide maximum sensitivity and give a tentative idea of potential inhibitors of early replicative steps such as adsorption or penetration. After one hour, cells were infected with 100 µL of appropriate viral dose per well [HSV-1 at a multiplicity of infection (MOI) of $10^4$ $TCID_{50}$ or HSV-2 at a MOI of $10^3$ $TCID_{50}$] using viral stock obtained in step 2 of Example 8. The infected cells were incubated with maintenance medium (DMEM with 2% FBS) for another 48 to 50 hours. When virus controls showed the maximum CPE, medium was aspirated and the cells were washed with 0.85% saline followed by staining with 0.1% crystal violet solution for 30 minutes. The staining solution was aspirated out and the plates rinsed using distilled water until all excess stain was washed away. The plates were allowed to dry for 24 hours. CPE was evaluated visually, after staining the plaques, and microscopically and graded according to the percentage of CPE inhibition as compared to controls. Results obtained are presented in Table 2.

TABLE 2

| Sample | % CPE inhibition (HSV-1) | | % CPE inhibition (HSV-2) | |
| --- | --- | --- | --- | --- |
|  | 50 µg/mL | 100 µg/mL | 50 µg/mL | 100 µg/mL |
| Sample 1 | − | − | + | − |
| Sample 2 | − | ++++ | ++++ | ++++ |
| Sample 3 | − | − | − | − |
| Sample 4 | + | ++ | + | ++++ |
| Sample 5 | − | − | − | − |
| Sample 6 | + | − | +++ | + |
| Sample 7 | − | − | − | − |
| Sample 8 | ++++ | ++++ | ++++ | ++++ |
| Sample 9 | − | − | − | − |
| Sample 10 | ++ | − | + | − |
| Sample 11 | ++++ | + | +++ | + |
| Sample 12 | − | − | + | − |
| Sample 13 | − | − | − | − |
| Sample 14 | − | − | − | − |
| Sample 15 | − | − | − | − |
| Sample 16 | ++ | − | + | − |
| Sample 17 | − | − | − | − |
| Sample 18 | + | ++ | ++ | +++ |
| Sample 19 | − | − | − | ++ |
| Sample 20 | ++++ | + | ++++ | ++++ |
| Sample 21 | − | + | ++++ | +++ |
| Sample 22 | +++ | ++++ | ++++ | ++++ |
| Sample 23 | ++++ | ++++ | ++++ | ++++ |
| Sample 24 | +++ | − | +++ | ++++ |
| Sample 25 | − | ++ | ++++ | ++++ |
| Sample 26 | − | − | − | +++ |

The results obtained with acyclovir are shown in Table 3.

TABLE 3

| Acyclovir conc. µg/mL | % CPE inhibition (HSV-1) | % CPE inhibition (HSV-2) |
| --- | --- | --- |
| 0.78 | + | nd |
| 1.5 | ++ | nd |
| 3.125 | +++ | + |
| 6.25 | +++ | ++ |
| 12.5 | ++++ | +++ |
| 25 | nd | ++++ |

The symbols used in the above tables 2 and 3 have the following meaning

| Symbols | % CPE inhibition | Symbols | % CPE inhibition |
| --- | --- | --- | --- |
| nd | not done; | − | 0-10% CPE inhibition; |
| + | 11-25% CPE inhibition; | ++ | 26-50% CPE inhibition; |
| +++ | 51-75% CPE inhibition; | ++++ | 76-100% CPE inhibition. |

Example 10

CPE Inhibition Assay—MTT Method $IC_{50}$ was determined for extracts which showed good dose response against both HSV-1 and HSV-2. $IC_{50}$ was estimated by CPE inhibition assay (MTT method).

The assay was designed to detect agents (in this case, the extracts) acting at any stage of the virus reproductive cycle. The assay was done as reported in World J. Gastroenterol., 2006, 12:4078-4081 incorporated herein by reference for its procedure.

This assay was performed as described in Example 9, for CPE inhibition assay-staining method, except that 3-(4,5-dimethylthiazol-2yl)-2,5-diphenyltetrazolium bromide (MTT) assay was carried out without staining of the cells with crystal violet staining. Vero cells (obtained in step 1 of Example 8) in 96-well flat-bottomed plates were treated with maintenance medium (DMEM with 2% FBS) that contained sample 1 of Example 1 or acyclovir for 1 hour. Then cells were infected with virus (using viral stock obtained in step 2 of example 8) at a MOI of 100 $TCID_{50}$. After 48 hour incubation at 37° C., viable cells were measured (absorbance at 570 nm was measured by using 96-well plate ELISA reader) by MTT assay. The data was analyzed by plotting a graph of sample concentrations (µg/ml) versus calculated % viability of Vero cells (treated with virus and controls), allowing quantification of changes in cell proliferation. The antiviral activity was determined according to the following formula:

$$\text{Antiviral activity} = \frac{(OD_T)_{HSV} - (OD_C)_{HSV}}{(OD_C)_{mock} - (OD_C)_{HSV}} \times 100$$

wherein:
- $(OD_T)_{HSV}$: absorbance measured with a concentration of extract in HSV infected cells;
- $(OD_C)_{HSV}$: refers to absorbance measured for the control untreated HSV-infected cells; and
- $(OD_C)_{mock}$: refers to absorbance measured for control untreated mock-infected cells.

$IC_{50}$ value was calculated from this data as concentration needed to inhibit half of the maximum cytopathic effect of HSV-1 and HSV-2.

Result: $IC_{50}$ value of sample 1 of Example 1 against HSV-1 was 15.48 µg/mL. $IC_{50}$ value of sample 1 of Example 1 against HSV-2 was 17 µg/mL.

Example 11

Cytotoxicity Assay

The assay was done as reported in World J. Gastroenterol., 2006, 12:4078-4081 incorporated herein by reference for its procedure.

Toxicity analysis was performed in order to assess whether any observed antiviral effects resulted from a general effect on cell viability. Vero cells (obtained in step 1 of example 8) for the toxicity analyses were cultured in 96-well plates and treated with extracts with the same schedule as used for antiviral evaluations without addition of virus. Viable cells were assayed using the MTT dye. Toxic effects of sample 1 of Example 1 were calculated as a percentage of the reduction of viable cells in the presence of the plant extract as compared to viable cells observed in the absence of plant extract. The following formula was used:

$$\text{Cytotoxicity} = \frac{\{A(\text{extract}) - A(\text{Blank})\}}{\{A(\text{Cell control}) - A(\text{Blank})\}} \times 100$$

wherein A represents absorbance measured at ELISA reader.

The 50% cell cytotoxic concentration ($CC_{50}$) was calculated from this data.

The selectivity index (SI), also referred to as therapeutic index, was evaluated as the ratio of $CC_{50}$ and $IC_{50}$ and the results obtained are given in Table 5. To determine if sample 1 of Example 1 has sufficient antiviral activity that exceeds its level of toxicity, SI was calculated according to $CC_{50}/IC_{50}$.

For present study SI value of >5 has been considered as effective for extracts. Results obtained are presented in Table 4.

TABLE 4

| Sample | *$IC_{50}$ (µg/mL) | $CC_{50}$ (µg/ml) | SI ($CC_{50}/IC_{50}$) |
|---|---|---|---|
| Sample 1 of Example 1 (against HSV-1) | 15.48 | 483.33 | 31.2 |
| Sample 1 of Example 1 (against HSV-2) | 17 | 483.33 | 28.4 |

*$IC_{50}$ value obtained from Example 10.

Example 12

Evaluation of the Effect of Sample 23 of Example 4 on HSV-1 and HSV-2 Replication at Different Time Points Post-Infection The objective of this study was to determine the stage of HSV-1/HSV-2 replication that may be blocked by sample 23 of Example 4. An antiviral drug candidate may specifically inhibit and target a virus at any stage of its replication cycle such as adsorption, fusion, uncoating, reverse transcription, integration, nucleic acid synthesis and maturation (Methods in Molecular Medicine, 1998, vol 10, 387-405). These stages occur at different time points in the virus life cycle spanning from 1 hour—initiation of adsorption to 24 hours—completion of one HSV replication cycle. Adsorption stage of the virus life cycle is the initial attachment of the herpes virus to host cells which involves interaction of gC and gD (conserved glycoproteins) on the virus with cell surface receptors such as heparin sulfate. Attachment stage of the virus life cycle is the stable attachment which allows close association of virus with the cell. The stage of the virus life cycle subsequent to the adsorption and attachment stages is known as the post infection stage.

Vero cells were seeded onto 96-well flat-bottomed plates at a density of $2.2 \times 10^4$ cells/well in 10% FBS-DMEM growth medium. After 20-24 hours, the confluent monolayers were infected with 100 µL/well of $1:10^4$ virus dilution (HSV-1 clinical strain) ($TCID_{50}$ $5.88 \times 10^6$/mL) or $1:10^3$ dilution of HSV-2 ($TCID_{50}$ $2.43 \times 10^6$/mL) and plates incubated for 1 hour at 37° C. and 5% $CO_2$. Two fold serial dilutions of sample 23 of Example 4 and acyclovir, were prepared in 2% FBS-DMEM maintenance medium to obtain eight concentrations 3.125, 6.25, 12.5, 25, 50, 100, 200 and 400 µg/mL and 100 µL of each dilution was added per well in triplicate at 0, 1, 3, 5, 7, 16 and 24 hours post infection. At 0 hour, sample 23 of Example 4 and acyclovir dilutions were added concurrently with the virus. Maintenance medium was added to the wells for virus control (virus dilution+maintenance medium) and cell control (maintenance medium only). The plates were further incubated for 48-50 hours at 37° C. Following incubation, the contents of the plate were discarded and the plate was washed with DMEM once. 100 µL/well of 1:10 dilution of the MTT reagent prepared in 2% FBS-DMEM maintenance medium was added to the plate and incubated for 4 hours until purple dye was visible. 100 µL of Detergent Reagent per well was then added. The plate was left in the 37° C., 5% $CO_2$ incubator overnight. After incubation, the plate cover was removed and absorbance measured in each well at 570 nm in the microplate plate reader (BIO-TEK, Synergy HT).

Observations for Studies Involving Herpes Simplex Virus, HSV-1:
- At 0 hour, corresponding to the adsorption stage, 52% antiviral activity was observed at 50 µg/mL, 77% at 100 µg/mL and 64% at 200 µg/mL.
- At 1 hour post infection (p.i), corresponding to the attachment stage, 80% antiviral effect was observed at 100 µg/mL and 64% at 200 µg/mL.
- At 3 hours p.i., corresponding to the initiation of replication, 90% antiviral effect was observed at 100 µg/mL and 70% at 200 µg/mL.
- At 5 hours p.i., corresponding to HSV viral DNA synthesis, 83% antiviral effect was observed at 100 µg/mL and 68% at 200 µg/mL.

At 7 hours p.i., corresponding to the later stages of HSV viral DNA synthesis, 77% antiviral effect was observed at 100 µg/mL and 73% at 200 µg/mL.

At 16 hours p.i., corresponding to the maximum efficiency of replication, 75% antiviral effect was observed at 100 µg/mL and 71% at 200 µg/mL.

At 24 hours p.i., corresponding to HSV virion egress (release of mature virions from the host cell after replication) 36% antiviral effect was observed at 100 µg/mL and 37% at 200 µg/mL.

Acyclovir showed potent antiviral effect against HSV-1 at all the concentrations between 3.125-200 µg/mL from 0-7 hours. This activity drastically reduced to about 17% at 16-24 hours corresponding to the later stages of replication and virion egress. Thus, the results of this study indicate that acyclovir was ineffective at the later stages of HSV-1 replication.

Conclusion: The antiviral activity of sample 23 of Example 4 against HSV-1 thus peaked at 3 hours p.i. This activity was potent from 0-16 hours p.i. and reduced considerably at 24 hours p.i.

Observations for Studies Involving Herpes Simplex Virus, HSV-2:

At 0 hour, corresponding to the adsorption stage, 77% antiviral activity was observed at 50 µg/mL, 76% at 100 µg/mL and 51% at 200 µg/mL.

At 1 hour p.i., corresponding to the attachment stage, 66% antiviral effect was observed at 100 µg/mL and 52% at 200 µg/mL.

At 3 hours p.i., corresponding to the initiation of replication, 74% antiviral effect was observed at 100 µg/mL and 55% at 200 µg/mL.

At 5 hours p.i., corresponding to HSV viral DNA synthesis, 79% antiviral effect was observed at 100 µg/mL and 63% at 200 µg/mL.

At 7 hours p.i., corresponding to the later stages of HSV viral DNA synthesis, 83% antiviral effect was observed at 100 µg/mL and 67% at 200 µg/mL.

At 16 hours p.i., corresponding to the maximum efficiency of replication and initiation of virion release, 83% antiviral effect was observed at 100 µg/mL and 67% at 200 µg/mL.

At 24 hours p.i., no antiviral effect was observed.

Acyclovir showed potent antiviral effect against HSV-2 at all the concentrations between 3.125-200 µg/mL from 0-7 hours. This activity was absent at 16-24 hours p.i. which corresponds to the later stages of replication and virion egress. Thus, the results of this study indicate that acyclovir was ineffective at the later stages of HSV-2 replication.

Conclusion: The antiviral activity of sample 23 of Example 4 against HSV-2 peaked at 7-16 hours p.i. This activity was potent from 0-16 hours p.i.

Example 13

Evaluation of Antiviral Activity of Sample 23 of Example 4 Against Herpes Simplex Viruses, HSV-1 and HSV-2 Prior to Infection In order for herpes viruses to enter a target cell, they must fuse their lipid membrane envelope with the lipid membrane of the cell. This complex viral entry mechanism is mediated by at least three conserved glycoprotein's (gC, gB and gD) and their ability to bind cell surface receptors such as nectins and herpes virus entry mediator (HVEM) (Cell. Mol. Life Sci, 2008, 65, 1653-1668). The objective of this pre-treatment assay was to establish whether sample 23 of Example 4 was able to cause viral inhibition by interacting with structures of the virion envelope such as the glycoprotein's or cell surface receptors such as heparan sulfate (HS) that are necessary for adsorption or entry into Vero cells.

Vero cells were seeded onto 24 well plates at a density of $1.8 \times 10^5$ cells/well. The plates were incubated for 20-24 hours at 37° C. and 5% $CO_2$. Serial two-fold dilutions of sample 23 of Example 4 and acyclovir, both at a concentration range of 3.125-400 µg/mL, were added to appropriate wells (200 µL/well) in duplicate and incubated at 37° C. and 5% $CO_2$ for 1 hour. Post one hour, these dilutions were aspirated out, Vero cells were washed once with PBS and then infected with 200 µL/well of HSV-1 virus suspension at a titer of $2.1 \times 10^8$ pfu/mL or HSV-2 virus suspension at a titer of $1.65 \times 10^7$ pfu/mL. The virus was allowed to adsorb for 1 hour at 37° C. and 5% $CO_2$ followed by a PBS wash. 1 mL overlay medium (1% carboxymethyl cellulose+2% FBS-DMEM) was then added to each well and the plates were further incubated at 37° C. and 5% $CO_2$ for 49 hours. Following incubation, the plates were washed with 0.85% saline and stained with 0.13% crystal violet. Viral plaques were enumerated and $IC_{50}$ value for sample 23 of Example 4 extract was calculated.

Figure 3:
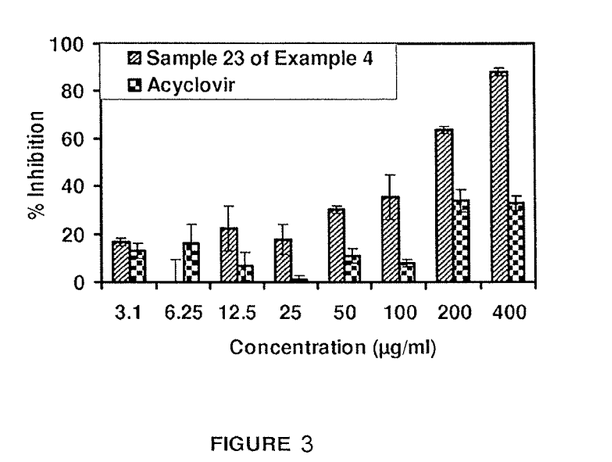
FIG. 3 depicts inhibitory activity of sample 23 of Example 4 against HSV-1 prior to infection in comparison with the inhibitory activity of acyclovir.

Result:

FIG. 3 illustrates significant inhibitory activity of Sample 23 of Example 4 from 200-400 µg/mL as indicated by 63-88% inhibition against HSV-1. The $IC_{50}$ value for sample 23 of Example 4 was calculated as 171.25 µg/ml against HSV-1. The observed inhibitory effect of sample 23 of Example 4 against HSV-1 was potent as compared with the weak inhibitory effect, 10-40%, exhibited by acyclovir at a concentration range of 3.125-400 µg/mL.

Figure 4:
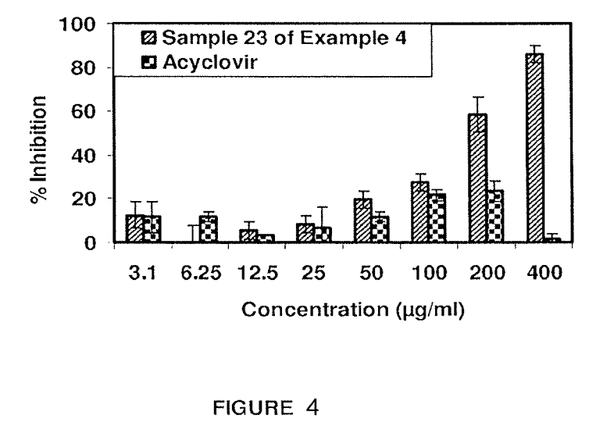
FIG. 4 depicts inhibitory activity of sample 23 of Example 4 against HSV-2 prior to infection in comparison with the inhibitory activity of acyclovir.

FIG. 4 illustrates 60-86% inhibition by Sample 23 of Example 4 at 200-400 µg/ml against HSV-2. The $IC_{50}$ value for sample 23 of Example 4 was calculated as 202.5 µg/ml against HSV-2. Acyclovir exhibited weak inhibitory effect, 10-20% at a concentration range of 3.125-400 µg/mL against HSV-2.

Conclusion:

Pre-treatment with sample 23 of Example 4 resulted in causing significant inhibition of HSV-1 and HSV-2 entry into Vero cells (adsorption and attachment) immediately after contact with the virus indicating prophylactic effect. This inhibitory effect was significantly more potent than that of acyclovir.

Example 14

Virus Adsorption Assay

There are many steps in a virus life cycle that can be targeted by potential antiviral product candidates such as adsorption, fusion, uncoating, reverse transcription, integration, nucleic acid synthesis and maturation. The results of the adsorption assay, will therefore help to establish the credibility of sample 23 of Example 4 to inhibit HSV-1 or HSV-2 at the adsorption stage of its infectious cycle wherein glycoprotein C (gC) and glycoprotein D (gD) on the virus interact with cell surface receptor glycosaminoglycans (GAGs) such as heparan sulfate (HS).

Vero cells were seeded onto 24 well flat bottomed plates at a concentration of $1.8 \times 10^5$ cells/well. The plates were incubated for 20-24 hours at 37° C. and 5% $CO_2$ until confluent monolayers were formed. Two-fold serial dilutions of sample 23 of Example 4 and acyclovir were prepared to yield concentrations ranging from 3.125-400 µg/mL. HSV-1 virus suspension at a concentration of $2.1 \times 10^8$ pfu/mL or HSV-2 at $1.65 \times 10^7$ pfu/mL were prepared.

Equal volumes of each dilution of sample 23 of Example 4/acyclovir and HSV-1/HSV-2 virus suspension were placed in sterile eppendorf tubes and the mixtures were incubated at 37° C. for 1 hour. 200 μL of these admixtures were then added to the Vero cell monolayers to allow the virus to adsorb in the presence of the extract for 1 hour at 37° C. and 5% $CO_2$. The plates were then washed once with PBS to remove the unbound virus and 1 mL overlay medium (1% carboxy methyl cellulose; CMC) prepared in 2% FBS-DMEM maintenance medium was added to each well. Further incubation for 49 hours at 37° C. and 5% $CO_2$, with regular monitoring was followed by 0.85% saline wash and staining with 0.13% crystal solution. Viral plaques were enumerated and the $IC_{50}$ value calculated.

Figure 5:
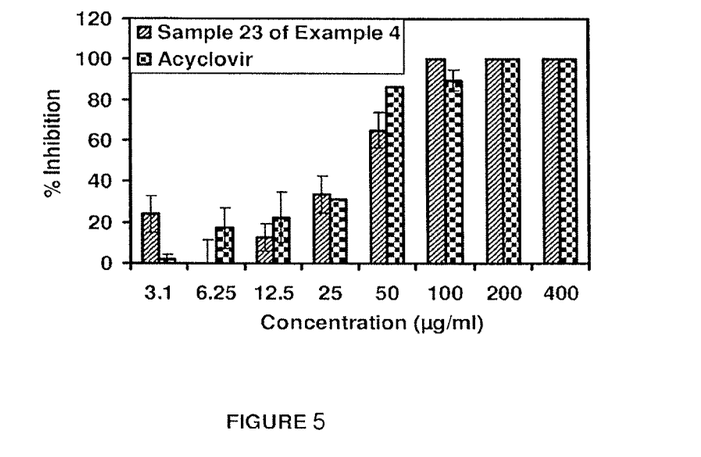
FIG. 5 depicts inhibitory effect of sample 23 of Example 4 on HSV-1 adsorption in comparison with the inhibitory effect of acyclovir.

Result:

FIG. 5 shows that sample 23 of Example 4 was able to cause 100% inhibition of HSV-1 virus adsorption from 100-400 μg/mL which decreased to 65% at 50 μg/mL. $IC_{50}$ for sample 23 of Example 4 is 44 μg/mL against HSV-1.

Figure 6:
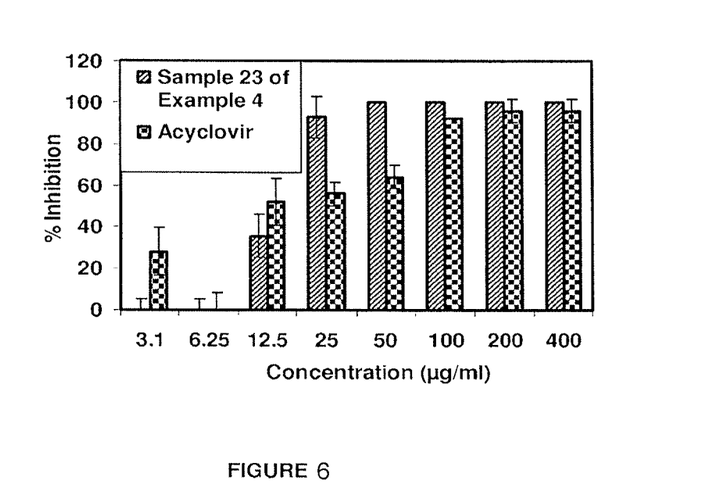
FIG. 6 depicts inhibitory effect of sample 23 of Example 4 on HSV-2 adsorption in comparison with the inhibitory effect of acyclovir.

FIG. 6 shows 100% inhibition of HSV-2 virus adsorption by sample 23 of Example 4 at 50-400 μg/mL against HSV-2 which decreased to 92% at 25 μg/mL $IC_{50}$ for sample 23 of Example 4 is 15 μg/mL against HSV-2.

The activity of sample 23 of Example 4 against HSV-1 and HSV-2 was marginally better than that of acyclovir. Sample 23 of Example 4 was effective when present both prior to and during the adsorption phase of HSV-1 and HSV-2 viral infection at the concentration range of 50-400 μg/mL and was not microscopically cytotoxic at these concentrations.

Example 15

Virus Penetration Assay

Penetration of HSV into host cells may be defined as a step subsequent to initial binding to the host cell surface which triggers fusion of the virion envelope with the plasma membrane. This requires multiple interactions, in a cascade like manner, involving various glycoproteins (gB, gD and gH/gL) and cell surface components (Cell. Mol. Life Sci, 2008, 65, 1653-1668). The objective of the virus penetration assay was to establish, in vitro whether sample 23 of Example 4 would inhibit HSV-1 and HSV-2 virus penetration into Vero cells.

Vero cells were seeded onto 24 well plates at a density of $1.8 \times 10^5$ cells/well. The plates were incubated for 20-24 hours at 37° C. and 5% $CO_2$ The confluent plates were placed at 4° C. for approximately half hour prior to start of experiment to enable Vero cells to acclimatize to the cold environment as the subsequent steps were carried out at 4° C. HSV-1 virus suspension at a titer of $2.1 \times 10^8$ pfu/mL or HSV-2 at $1.65 \times 10^7$ pfu/mL was prepared and 200 μL was added to the confluent monolayers. The cells were incubated at 4° C. for 2 hours to allow viral attachment. Serial two-fold dilutions of sample 23 of Example 4 and acyclovir both at a concentration range of 3.125-400 μg/mL were added to appropriate wells at room temperature and plates incubated at 37° C. and 5% $CO_2$ for 10 minutes. Dilutions of sample 23 of Example 4 and acyclovir were then aspirated out and the cell monolayer briefly washed with PBS (pH 3.75) to inactivate virions that had not penetrated the cells. Subsequently cells were washed with PBS (pH 11.0), to neutralize the acidic pH environment. 1 mL overlay medium (1% CMC in 2% FBS-DMEM maintenance medium) was then added to each well and the plates were incubated at 37° C. for 48-50 hours. The plates were then washed with 0.85% saline and stained with 0.13% crystal violet. Plaques were enumerated and $IC_{50}$ value for sample 23 of Example 4 was calculated.

Figure 7:
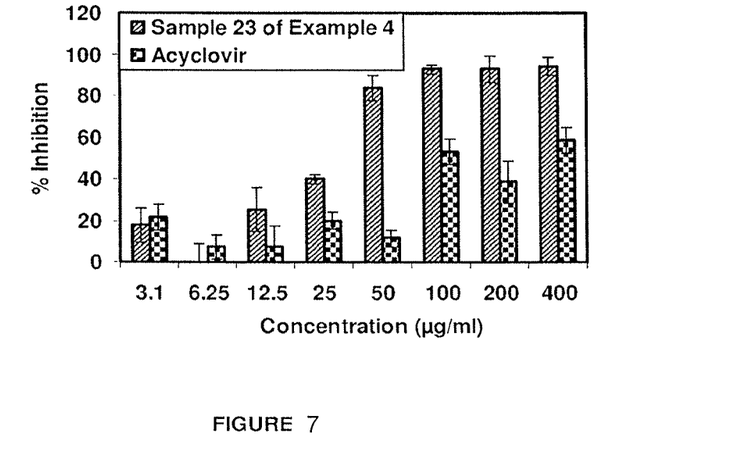
FIG. 7 depicts inhibitory activity of sample 23 of Example 4 against HSV-1 penetration in comparison with the inhibitory activity of acyclovir.

Result:

FIG. 7 demonstrates 80-95% inhibition of HSV-1 virus by sample 23 of Example 4 from 50-400 μg/mL which decreased at the lower concentrations (3.125-25 μg/mL). The $IC_{50}$ of sample 23 of Example 4 against HSV-1 virus was calculated to be 30 μg/mL.

Figure 8:
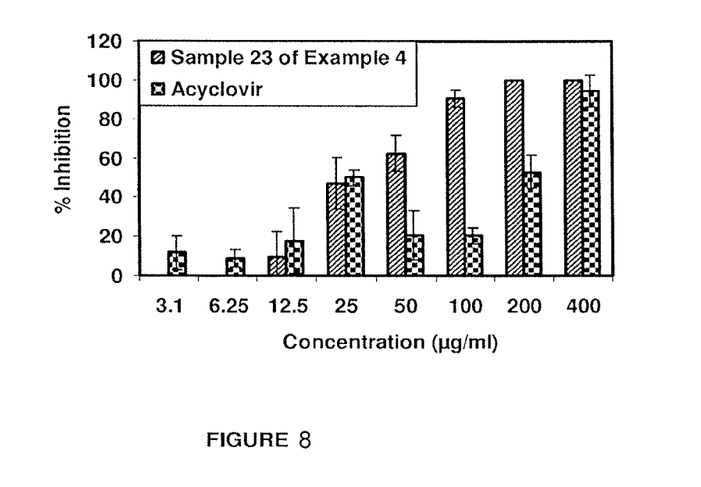
FIG. 8 depicts inhibitory activity of sample 23 of Example 4 against HSV-2 penetration in comparison with the inhibitory activity of acyclovir.

FIG. 8 shows 100% inhibition of HSV-2 virus by sample 23 of Example 4 at 200-400 μg/mL which decreased to 90% at 100 μg/mL and 71% at 50 μg/mL. The $IC_{50}$ of sample 23 of Example 4 against HSV-2 virus was calculated to be 36.1 μg/mL.

Acyclovir showed weak to moderate inhibitory activity against HSV-1 and HSV_2 as compared to sample 23 of Example 4.

Conclusion:

The results indicate that sample 23 of Example 4 was able to significantly inhibit HSV-1 and HSV-2 virus penetration into Vero cells as compared to acyclovir which did not strongly inhibit this step of HSV-1 and HSV-2 virus entry into host Vero cells.

Example 16

Evaluation of the Virucidal Activity of Sample 23 of Example 4 Against HSV-1 and HSV-2

In the virucidal assay, the continuous presence of an antiviral drug may be frequently required for blocking infectivity of viral particle for cultured cells and dilution of the virus-extract complexes may dissociate, releasing infectious virus (Antiviral research, 2010, 86, 196-203). If a sample is unable to reduce virus infectivity at the $IC_{50}$ or other potent concentrations then the antiviral activity is not related to its virucidal ability. The objective of this study was to evaluate in vitro, if the inhibitory activity of sample 23 of Example 4 against HSV-1 and HSV-2 is due to its antiviral effect or virucidal effect.

Vero cells were seeded onto 24 well flat-bottomed plates at a concentration of $1.8 \times 10^5$ cells/well. The plates were incubated for 20-24 hours at 37° C. and 5% $CO_2$. Two-fold serial dilutions of sample 23 of Example 4 and acyclovir were prepared to yield concentrations ranging from 25-400 μg/mL. HSV-1 virus suspension at a concentration of approximately $10^{10}$ pfu/mL and HSV-2 at $10^9$ pfu/ml were prepared. Equal volumes of each dilution of sample 23 of Example 4/acyclovir and HSV-1/HSV-2 virus suspension were placed in sterile eppendorf tubes and the mixtures were incubated at 37° C. for 1 hour. These admixtures were then diluted ten-fold (1:100) to yield a final concentration range of 0.25-4 μg/ml corresponding to 25-400 μg/ml. 200 μl of these admixtures were then added to the Vero cell monolayers to allow the virus to adsorb for 1 hour at 37° C. and 5% $CO_2$. The plates were then washed once with PBS to remove the unbound virus and 1 ml overlay medium (1% carboxy methyl cellulose; CMC) prepared in 2% FBS-DMEM maintenance medium was added to each well. Further incubation for 48-50 hours at 37° C. and 5% $CO_2$, was followed by 0.85% saline wash and staining with 0.13% crystal solution. Viral plaques were then enumerated.

Figure 9:
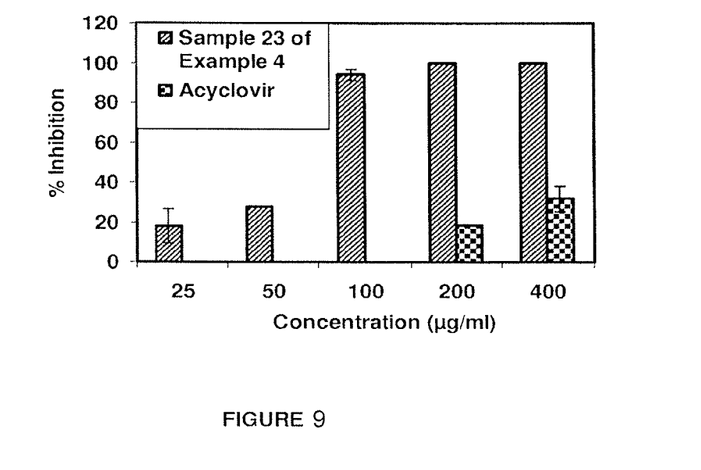
FIG. 9 depicts virucidal effect of sample 23 of Example 4 against HSV-1 in comparison with the virucidal effect of acyclovir.

Result:

FIG. 9 exhibits 100% virucidal effect by sample 23 of Example 4 against HSV-1 at 200-400 μg/mL and 94% inhibition at 100 µg/mL. Acyclovir showed weak virucidal effect ranging from 0-32% at concentration range of 25-400 µg/mL against HSV-1.

Figure 10:
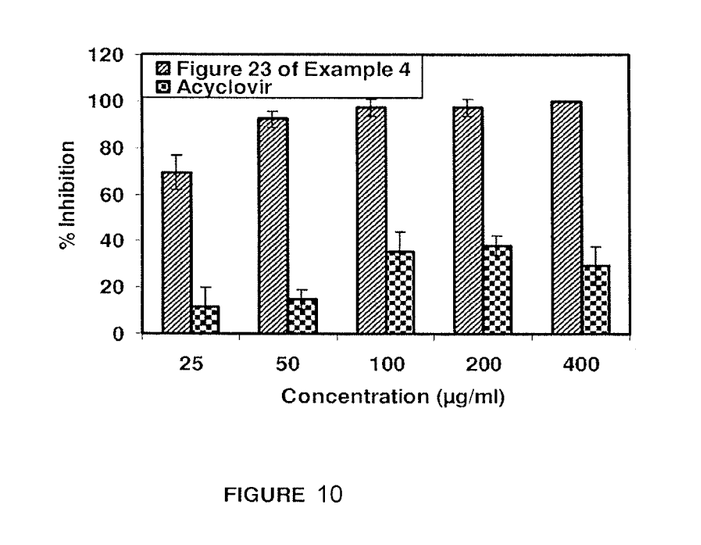
FIG. 10 depicts virucidal effect of sample 23 of Example 4 against HSV-2 in comparison with the virucidal effect of acyclovir.

FIG. 10 shows 100% virucidal effect by sample 23 of Example 4 against HSV-2 at 400 µg/mL and 92-97% inhibition at 50-200 µg/mL. Acyclovir showed weak virucidal effect ranging from 11-38% at concentration range 25-400 µg/mL against HSV-2.

Conclusion

Sample 23 of Example 4 exhibited strong virucidal effect against HSV-1 and HSV-2 viruses as compared to acyclovir.

In Vivo Antiviral Assays

Animals used in the experiments were housed and cared for, in accordance with the Guidelines in force published by CPCSEA (Committee for the Purpose of Control and Supervision of Experiments on Animals), Tamil Nadu, India. Procedures using laboratory animals were approved by the IAEC (Institutional Animal Ethics Committee) of Piramal Healthcare Limited, Goregaon, Mumbai, India.

Example 17

Mouse HSV-1 Zosteriform Spread Infection Model

The assay was done as reported in Antimicrobial Agents and Chemotherapy, June 2002, p. 1766-1772, incorporated herein by reference for its procedure.

Balb/c female mice of 6 to 8 weeks which are non-pregnant and nulliparous were used for the study. All the animals were shaved on right mid dorsal area using electric hair clipper and few horizontal scarification was done on shaved area using sterile 26 gauge needle, just before viral challenge.

Prior to viral challenge, the scarified area of each mouse was cleaned with a cotton swab soaked in 70% alcohol followed by clearing the area using cotton swab soaked in sterile DMEM. Mice were then infected onto the scarified area with HSV-1 virus containing $8.27 \times 10^3$ pfu/animal. Animals received Formulation IA, Formulation IB, Formulation IC/acyclovir/placebo by topical administration at the site of infection at 1 hour of post infection. Animals were treated three times a day with the treatment intervals of 4 hours. All animals in all groups were treated for 5 days. Placebo (cream base) and acyclovir (225 mg/kg/day) treated animals served as controls and virus control group received no treatment.

The following formulations, as described in Example 6, were evaluated:
 (a) Formulation IA
 (b) Formulation IB
 (c) Formulation IC Formulation IA, Formulation IB and Formulation IC were applied topically thrice daily for a 5 day period. 15 mg of Formulation IA correspond to 225 mg/kg dose; 15 mg of Formulation IB correspond to 450 mg/kg dose; 15 mg of Formulation IC correspond to 675 mg/kg dose and 25 mg of Formulation IB correspond to 750 mg/kg dose evaluated in the animals.

The animals were assessed daily for morbidity, mortality and the site of infection for a period of 21 days post infection.

The severity of the viral disease (extravaginal signs of disease) was quantified using a well-established lesion score scale, as follows:
 0: no apparent infection;
 1: vesicle formation;
 2: formation of large patches of zoster;
 3: confluent zoster band;
 4: hind limb paralysis Zosteriform lesions refer to band like unilateral skin lesions located along the cutaneous distribution of a spinal or a branch of the trigeminal nerves.

Observations:

Animals belonging to all dose groups started showing earlier sign of zosteriform lesions by day 2 post infection.

1 Group treated with placebo:
 (a) Animals started showing severity of infection by day 6, post infection.
 (b) All of the mice died by day 8, post infection.
2 Group treated with acyclovir:
 (a) All mice recovered from zosteriform lesions by day 7, post infection.
 (b) None of the mice died during the experiment.
3 Group kept untreated (infection control):
 (a) Animals started showing severity of infection by day 6, post infection
 (b) All of the mice died by day 10, post infection.
4 Group treated with Formulation IB (750 mg/kg/day):
 (a) Mice treated with Formulation IB (750 mg/kg/day) showed 90% survival rate.
 (b) Surviving animals recovered from zosteriform lesions by day 9, post infection.
5 Group treated with Formulation IC (675 mg/kg/day):
 (a) Mice treated with Formulation IC at 675 mg/kg/day showed 80% survival rate.
 (b) Surviving animals recovered from zosteriform lesions by day 10, post infection.
6 Group treated with Formulation IB (450 mg/kg/day):
 (a) Mice treated with Formulation IB at 450 mg/kg/day showed 60% survival rate.
 (b) Surviving animals recovered from zosteriform lesions by day 10, post infection.
7 Group treated with Formulation IA (225 mg/kg/day):
 (a) Mice treated with Formulation IA at 225 mg/kg/day showed 20% survival rate. Most of the mortality occurred within day 8, post infection.
 (b) Surviving animals recovered from zosteriform lesions by day 9, post infection.

Result: Formulation IB and formulation IC exhibited good antiviral activity at higher concentrations, 750 and 675 mg/kg/day in the mouse HSV-1 zosteriform spread infection model.

Example 18

Mouse Vaginal Model of HSV-2 Infection

The assay was done as reported in Antiviral Research, 2006, 69:77-85, incorporated herein by reference for its procedure.

Balb/c female mice of 6 to 8 weeks, non-pregnant and nulliparous were used for the study. Female BALB/c mice were used for vaginal inoculation with HSV-2. Five days prior to intravaginal (IVAG) challenge, mice were injected subcutaneously (sc) with 2 mg of progesterone (Depo-Provera®; Pfizer, Belgium) in the upper back, using a 29-gauge needle. On the day of challenge, mice were inoculated intravaginally with $1.14 \times 10^5$ pfu of HSV-2. IVAG administrations of virus were via a micropipette in a total volume of 20 µL DMEM. Animals received Formulation IA, Formulation IB, Formulation IC/acyclovir/placebo intravaginally by topical administration 30 minutes post infection. Animals were treated three times a day with a treatment interval of 4 hours. All animals in all groups were treated for 5 days. Acyclovir (225 mg/kg/day) was included as positive control. Placebo control animals received base cream (placebo) at the same time-point and virus control group received no treatment.

The following formulations, as described in Example 6, have been evaluated:
(a) Formulation IA
(b) Formulation IB
(c) Formulation IC Formulation IA, Formulation IB and Formulation IC were applied topically thrice daily for a 5 day period. 15 mg of Formulation IA correspond to 225 mg/kg dose; 15 mg of Formulation IB correspond to 450 mg/kg dose and 15 mg of Formulation IC correspond to 675 mg/kg dose evaluated in the animals.

The animals were assessed daily for extravaginal disease signs and survival for a period of 21 days post infection.

The severity of the viral disease (extravaginal signs of disease) was quantified using a well-established lesion score scale, as follows:
0: no apparent infection;
1: few isolated papules and slight redness of extravaginal tissue;
2: few isolated papules, ulcers, and/or eschar and/or swelling and redness of extravaginal tissue;
3: multiple fused ulcers/eschars, moderate swelling and redness of extravaginal tissue with extension to surrounding tissue;
4: ulceration with severe redness and swelling of extravaginal tissue with extension to surrounding tissue, rear leg paralysis Observations:
1 Group treated with placebo:
(a) The earliest sign of extravaginal infection occurred on day 7.
(b) 90% of the mice died by day 14.
2 Group treated with acyclovir:
(a) None of the mice showed signs of extravaginal disease.
(b) None of the mice died during the experiment.
3 Group treated with Formulation IA (225 mg/kg/day):
(a) Mice treated with 225 mg/kg/day of Formulation I showed 90% survival rate.
(b) One out of ten mice showed appearance of clinical lesion by day 8, post infection. This animal died later on. Rest all other animals did not exhibit any characteristic signs of virus-induced extravaginal disease at any time during the experiment.

4 Group treated with Formulation IB (450 mg/kg/day):
(a) Mice treated with 450 mg/kg/day of extract of Formulation IB showed 90% survival rate.
(b) Two out of ten mice showed appearance of clinical lesion by day 14, post infection. One of these animals died later on. Rest all other animals did not exhibit any characteristic signs of virus-induced extravaginal disease at any time during the experiment.
5 Group treated with Formulation IC (675 mg/kg/day):
(a) None of the mice showed signs of extravaginal disease.
(b) None of the mice died during the experiment.

Result: Formulation IA, formulation IB and formulation IC exhibited antiviral activity at 225, 450 and 675 mg/kg/day in the mouse vaginal model of HSV-2 infection.

We claim:

1. A method of treating a viral infection caused by herpes simplex virus in a human in need thereof comprising administering to the human a composition comprising a therapeutically effective amount of an extract of *Ficus arnottiana*, and a pharmaceutically acceptable carrier.

2. The method as claimed in claim 1, wherein the extract of the plant *Ficus arnottiana* is prepared from the stem of the plant.

3. The method as claimed in claim 1, wherein the extract of the plant *Ficus arnottiana* is prepared from the bark of the plant.

4. The method as claimed in claim 1, wherein the extract of the plant *Ficus arnottiana* is prepared from the twig of the plant.

5. The method as claimed in claim 1, wherein the extract of the plant *Ficus arnottiana* contains one or more biomarkers.

6. The method as claimed in claim 5, wherein the bioactive marker is phlorizin or 5,7,4'-trihydroxyflavone or a mixture thereof.

7. The method as claimed in claim 6, wherein the bioactive marker is phlorizin.

8. The method as claimed in claim 6, wherein the bioactive marker is 5,7,4'-trihydroxyflavone.

9. The method as claimed in claim 1, wherein the composition comprises 5% to 50% (w/w) of the extract of *Ficus arnottiana*.

10. The method, as claimed in claim 1, wherein the viral infection is caused by HSV-1.

11. The method as claimed in claim 1, wherein the viral infection is caused by HSV-2.

* * * * *